United States Patent [19]

Poliac

[11] Patent Number: 5,993,394
[45] Date of Patent: Nov. 30, 1999

[54] SEGMENTED ESTIMATION METHOD

[75] Inventor: Marius O. Poliac, St. Paul, Minn.

[73] Assignee: Medwave, Inc., Arden Hills, Minn.

[21] Appl. No.: 09/059,157

[22] Filed: Apr. 13, 1998

Related U.S. Application Data

[62] Division of application No. 08/690,617, Jul. 31, 1996, Pat. No. 5,738,103.

[51] Int. Cl.$^6$ ...................................................... A61B 5/02
[52] U.S. Cl. ........................................... 600/485; 600/500
[58] Field of Search ................................... 600/485–486, 600/490–495, 499–503, 481

[56] References Cited

U.S. PATENT DOCUMENTS 5,181,515  1/1993  Negishi ................................... 128/672
5,533,511  7/1996  Kaspari et al. ......................... 128/672

*Primary Examiner*—Cary O'Connor
*Assistant Examiner*—Ryan Carter
*Attorney, Agent, or Firm*—Kinney & Lange, P.A.

[57] ABSTRACT

A method for determining blood pressure of an artery includes the steps of applying a pressure to the artery, sensing pressure data produced by the artery and deriving parameters for the sensed pressure data. The parameters are utilized for generating a first blood pressure value estimate using a first function of the parameters based upon a first range of pressure values and by generating at least one second blood pressure estimate using at least one second parameter function based upon a second blood pressure estimate using at least one second parameter function based upon a second pressure range different from the first pressure range. A blood pressure value is determined based upon the first blood pressure estimate and said at least one second blood pressure estimate.

5 Claims, 6 Drawing Sheets

SEGMENTED ESTIMATION METHOD

CROSS-REFERENCE TO RELATED APPLICATION

This application is a divisional of application Ser. No. 08/690,617, that was filed on Jul. 31, 1996, now U.S. Pat. No. 5,738,103.

BACKGROUND OF THE INVENTION

The present invention relates to methods for calculating blood pressure of an artery. In addition, the present invention relates to a method for ascertaining a relationship between at least one preselected parameter of at least one sensed pressure waveform and a blood pressure value for use in determining the blood pressure value.

Blood pressure has been typically measured by one of four basic methods: invasive, oscillometric, auscultatory and tonometric. U.S. patent application Ser. No. 08/388,751, entitled "METHOD AND APPARATUS FOR CALCULATING BLOOD PRESSURE OF AN ARTERY" and U.S. patent application Ser. No. 08/227,506 entitled "CONTINUOUS NON-INVASIVE BLOOD PRESSURE MONITORING SYSTEM", both of which are assigned to Medwave, Inc. (herein incorporated by reference), describe a novel non-invasive method for continuously measuring blood pressure without causing discomfort to a patient. The novel method involves non-invasively sensing amplitude and shape of the blood pressure pulses within the underlying artery to create signals representing the amplitude of the sensed blood pressure pulses. Based upon the sensed signals representing the sensed amplitude and shape of the blood pressure pulses, wave shape information is determined by measuring the amplitude and shape versus time of individual cardiac cycles. Parameter values derived from the sensed signals and the wave shape information are used by a microprocessor to calculate systolic, diastolic and mean blood pressures. However, it has been extremely difficult to ascertain a single function that accurately predicts blood pressure values based upon the derived parameter values. As a result, the use of a single function to calculate blood pressure values from the derived parameters has been extremely error prone.

SUMMARY OF THE INVENTION

The present invention is a method for determining blood pressure of an artery. The method includes the steps of applying pressure to the artery, sensing pressure produced by the artery and deriving parameters from the sensed pressure data. The method utilizes the derived parameters to generate a first blood pressure estimate using a first parameter function based upon a first pressure range and to generate at least one second blood pressure estimate using at least one second parameter function based upon a second range different from the first range. The blood pressure value is determined based upon the first blood pressure estimate and said at least one second blood pressure estimate.

The present invention is also a method for ascertaining a relationship between at least one factor and a corresponding result for use in estimating the result from at least one sensed factor value. More specifically, the present invention relates to a method for ascertaining a relationship between at least one preselected parameter of at least one sensed pressure waveform and a blood pressure value for use in determining the blood pressure value. According to one preferred embodiment of the present invention, a first function is ascertained based upon known blood pressure values and corresponding values of at least one preselected parameter. The first function estimates the blood pressure value based on said at least one preselected parameter. Possible blood pressure values are segmented into a plurality of ranges. For each range, a second function based upon known blood pressure values within each range and corresponding sensed values of said at least one preselected parameter is ascertained. Each second function estimates the blood pressure value based on said at least one preselected parameter. In one preferred embodiment, an estimate provided by the first function determines which of the second functions is used to determine the blood pressure value. In another preferred embodiment, a weighting function is ascertained for each second function dependent upon estimated blood pressure values of the first function. Using this method, the relationship between said at least one preselected parameter and the blood pressure value is a summation of each weighting function multiplied by its corresponding second function.

DETAILED DESCRIPTION OF THE PREFERRED EMBODIMENTS

I. Overview

Figure 1:
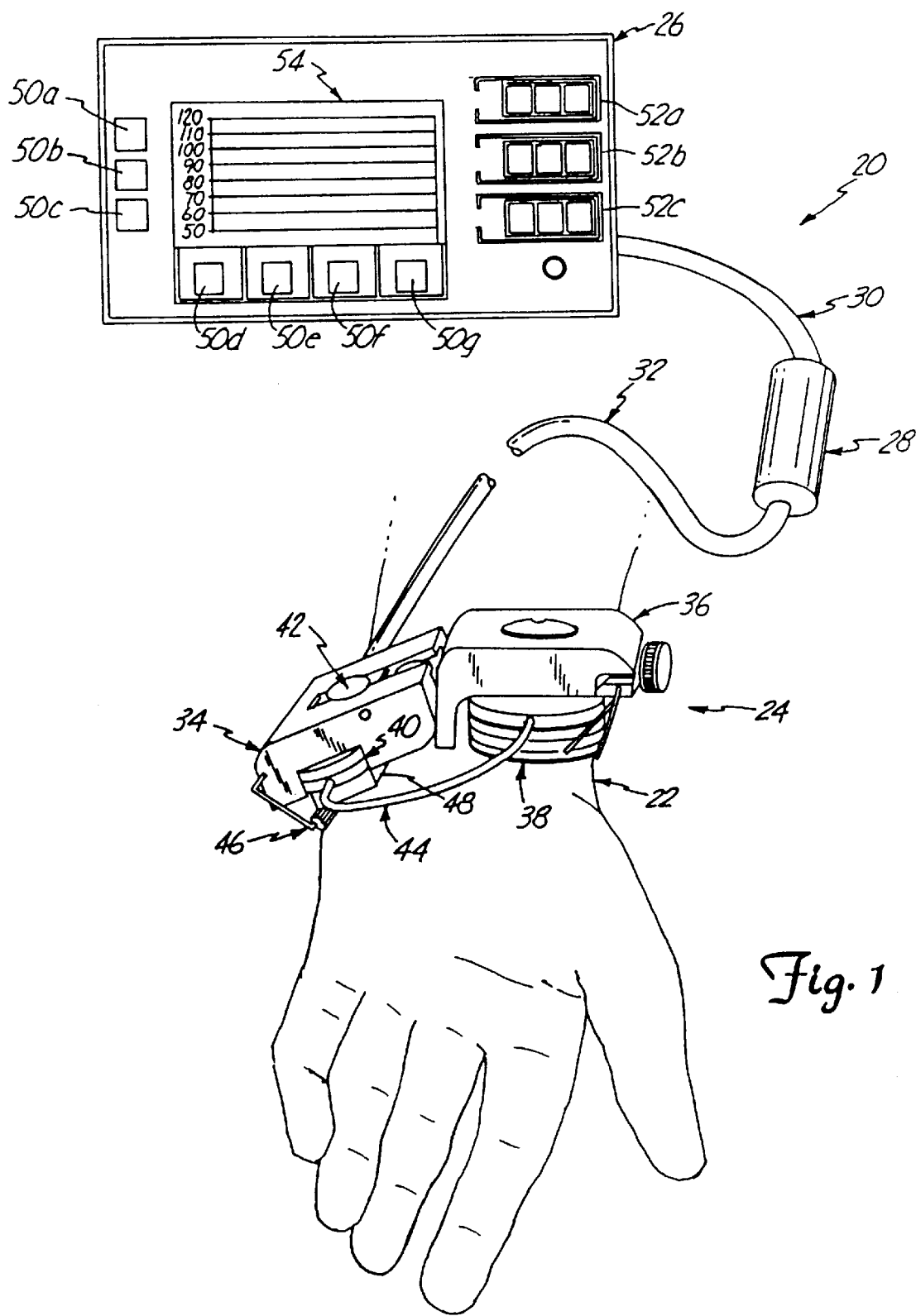
FIG. 1 is a perspective view of a blood pressure monitoring system having a sensor assembly mounted upon the wrist of a patient.

FIG. 1 illustrates blood pressure monitoring system 20 for measuring and displaying blood pressure within an underlying artery within wrist 22 of a patient. Monitoring system 20 includes wrist assembly 24, monitor 26, cylinder 28, cable 30 and cable 32.

Wrist assembly 24 is mounted on wrist 22 for applying a varying hold down pressure to an artery within wrist, and for sensing blood pressure waveforms produced in the artery. Wrist assembly 24 includes swivel mount 34, hold down assembly 36, sensor interface assembly 38, waveform pressure transducer 40, hold down pressure transducer 42, connection tube 44, wrist mount 46 and wrist pad 48.

Cylinder 28, under the control of monitor 26, supplies fluid pressure through cable 32 to wrist assembly 24 to produce the varying hold down pressure. Cylinder 28 includes a movable piston which is driven by stopper motor or linear actuator.

Electrical energization to wrist assembly 24 and pressure waveform sensor signals to monitor 26 are supplied over electrical conductors extending between monitor 26 and wrist assembly through cable 30, cylinder 28 and cable 32. Drive signals to cylinder 28 are supplied from monitor conductors within cable 30.

Monitor 26 receives the pressure waveform sensor signals from wrist assembly 24, digitizes the signals to produce pressure waveform data for a plurality of beats, and performs waveform analysis on the data. The waveform analysis extracts a plurality of waveform parameters, which preferably include waveform shape, relative amplitude and gain parameters. From the waveform parameters, monitor 26 calculates or otherwise derives blood pressure values, such as mean blood pressure, diastolic blood pressure and systolic blood pressure. Monitor 26 then displays the derived blood pressure values.

As shown in FIG. 1, monitor 26 includes control switches or input keys 50a–50g, digital displays 52a–52c and display screen 54. Input keys 50a–50c comprise hard keys for controlling monitor 32. Input keys 50d–50g consist of software programmable keys which are adaptable for various functions. Digital displays 52a–52c continually display systolic, diastolic and mean blood pressure, respectively. Display screen 54 displays the blood pressure pulse waveforms and prompts to guide the operator.

In operation, sensor interface assembly 38 is positioned over the radial artery. Wrist mount 46 maintains the position of wrist assembly 24 including sensor interface assembly 38 on wrist 22. In response to fluid pressure supplied from cylinder 28 through cable 32, hold down assembly 36 applies force and moves sensor interface assembly 38 to vary the pressure applied to wrist 22 above the radial artery.

As this pressure is varied, distinct arterial pressure waveforms are exhibited by the blood pressure pulse within the underlying artery. Each waveform corresponds to a cardiac cycle. Each arterial pressure waveform or shape is obtained by sensing and measuring pressures exhibited by the pulse of the underlying artery versus time during an individual cardiac cycle. Arterial pressure applied to sensor interface assembly 38 and is transferred as a fluid pressure from interface assembly 38 to waveform pressure transducer 40 through tube 44. The electrical sensor signals from transducer 40 are supplied to monitor 26 for digitization and analysis.

The amplitude of each sensed waveform is a function of the applied pressure applied to the artery by sensor interface assembly 38 and the amplitude of the arterial pulse. The shape characteristics of at least one waveform and other parameters derived from the sensed waveforms are used by digital signal processing circuitry of monitor 26 to determine systolic, mean and diastolic pressure. The calculated pressures are displayed by displays 52a–52c and display screen 54.

Blood pressure monitoring system 20 calculates a systolic blood pressure valve (S), a mean blood pressure (M) and a diastolic blood pressure (D) based upon the following formulas:

$$M = F_m(P_1^m, \ldots, P_n^m, C_1^m, \ldots, C_n^m)$$

$$S = F_s(P_1^s, \ldots, P_n^s, C_1^s, \ldots, C_n^s)$$

$$D = F_d(P_1^d, \ldots P_n^d, C_1^d, \ldots C_n^d)$$

wherein $F_m$, $F_s$, $F_d$ are linear or non-linear functions, $P_1^m$, $P_1^s$, $P_1^d$, ..., $P_n^m$, $P_n^s$, $P_n^d$ are parameters derived from waveform pressure amplitudes and $C_1^m$, $C_1^s$, $C_1^d$, ..., $C_n^m$, $C_n^s$, $C_n^d$ are coefficients obtained during training processes based upon clinical data. The parameters P, may be calculated from shape characteristics of the waveform or from functions such as curves based upon relationships between particular points of several waveforms. The parameters may be further based upon hold down pressure values and time periods between particular points on the waveforms. The values $C_1^m$, $C_1^s$, $C_1^d$, ..., $C_n^m$, $C_n^s$, $C_n^d$ are ascertained during training processes and represent the relationship between the parameters $P_1^m$, $P_1^s$, $P_1^d$, ..., $P_n^m$, $P_n^m$, $P_n^d$, respectively.

Parameters

Figure 2:
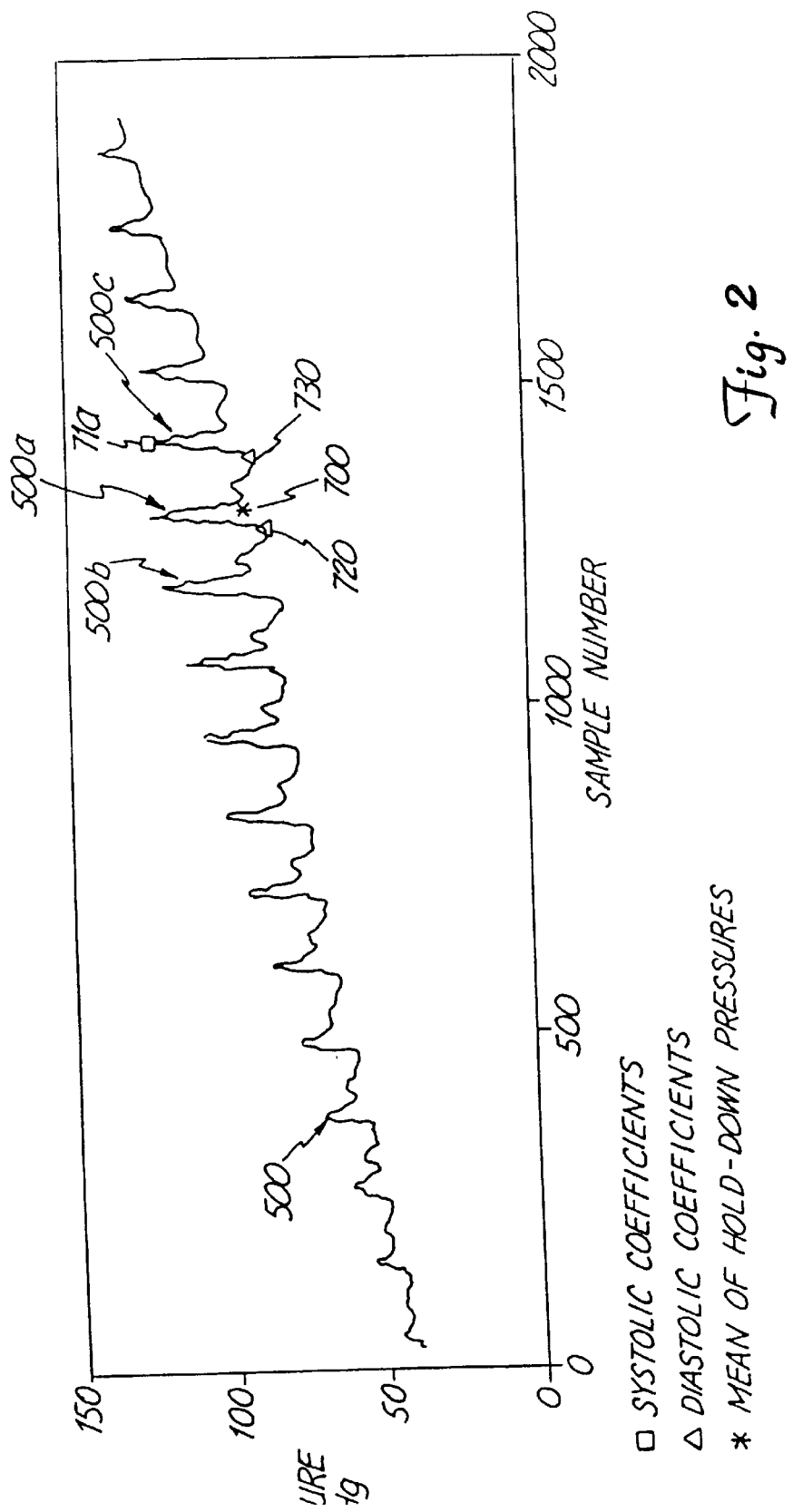
FIG. 2 is a graph illustrating blood pressure waveforms.
Figure 3:
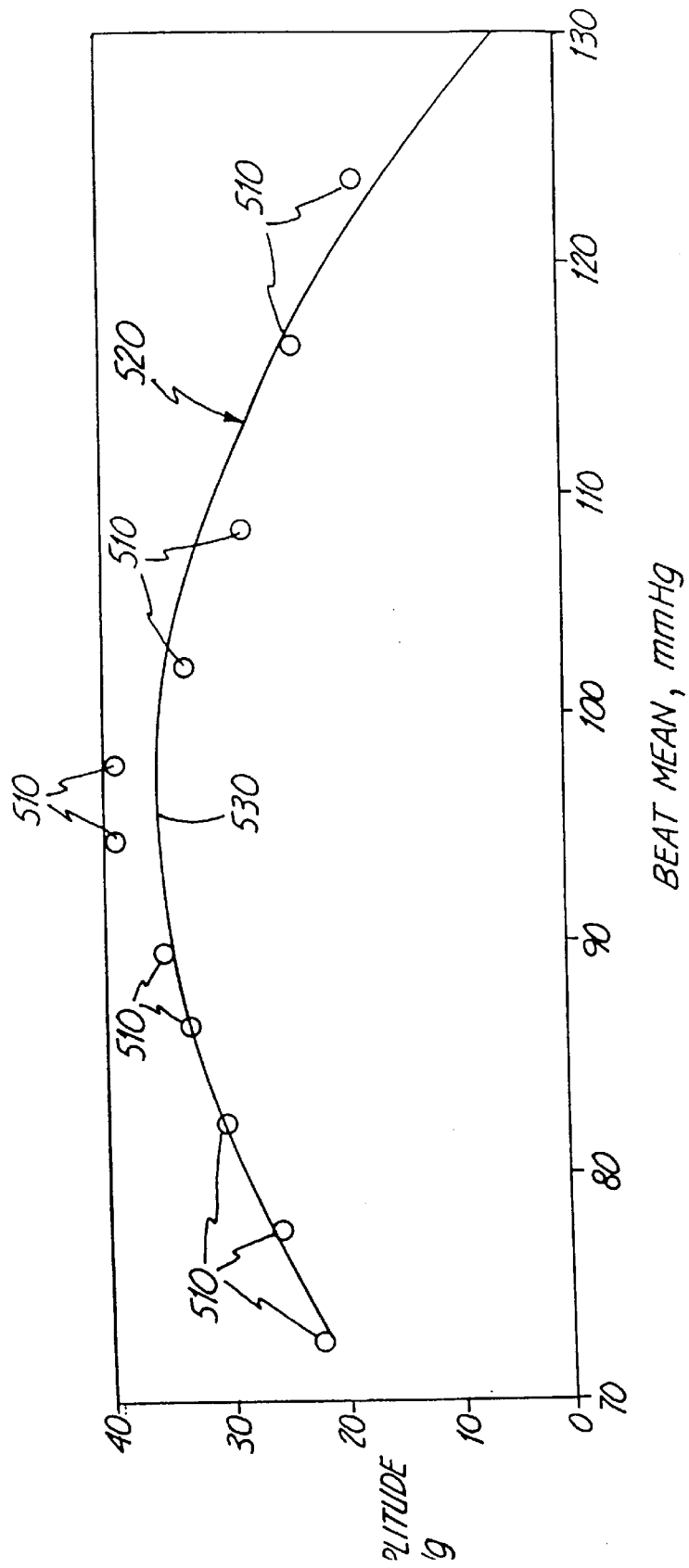
FIG. 3 is a graph illustrating a curve fit from points taken from the waveforms of FIG. 2.
Figure 4:
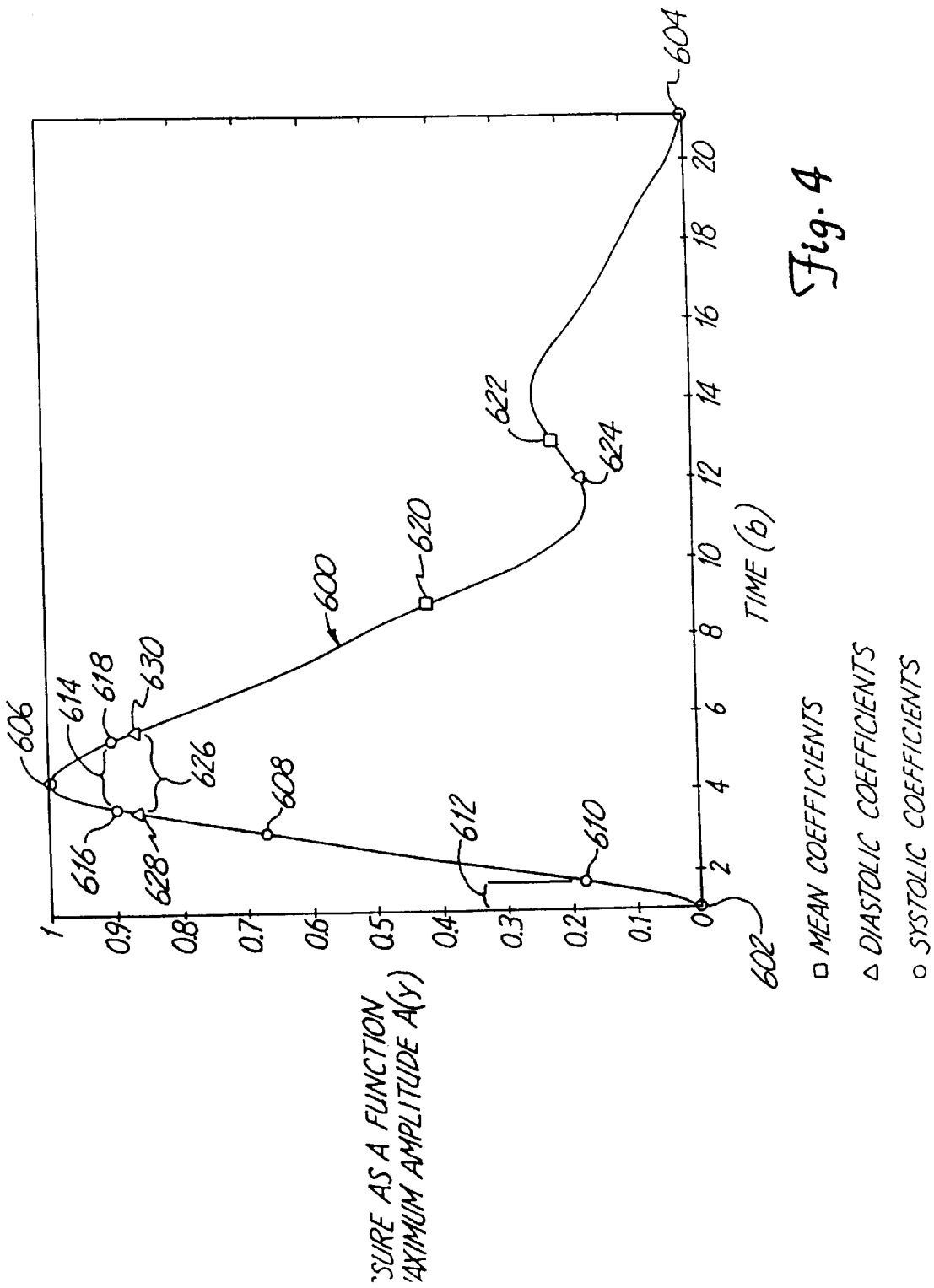
FIG. 4 is a graph illustrating a corrected and scaled waveform taken from the waveforms of FIG. 2.

FIGS. 2, 3 and 4 illustrate representative parameters which may be used to calculate blood pressure values. FIG. 2 illustrates a sample series of waveforms exhibited by the underlying artery as a varying pressure is applied over time. The vertical scale indicates pressure in mmHg while the horizontal scale indicates individual sample points at which the blood pressure values exerted by the pulse are measured over time. In the preferred embodiment, transducer 40 produces continuous electrical signals representing waveform pressures which are sampled 128 times per second.

In the preferred embodiment, the hold down pressure applied by hold down pressure assembly 36 to sensor interface assembly 38 (shown in FIG. 1) is swept over a preselected range of increasing hold down pressures. Preferably, the sweep range of hold down pressures is begun at approximately 20 mmHg. The hold down pressure applied by hold down pressure assembly 36 is then steadily increased until a waveform having the largest maximum pressure amplitude is sensed. In other words, the holddown pressure applied by holddown pressure assembly 36 is steadily increased until at least one individual waveform having a corrected maximum pressure amplitude less than the corrected maximum pressure amplitude of the immediately preceding waveform is sensed. Due to the time presently required for sensing and detecting the maximum pressure amplitude of each waveform or beat, the identification of the waveform having the largest maximum pressure amplitude typically does not occur until two individual waveforms have been sensed following the sensed waveform having the largest pressure amplitude. Holddown pressure assembly 36 preferably increases the pressure being applied to the underlying artery at a steadily increasing rate such that no greater than two heart beats or waveforms are sensed by monitoring system 20 after monitoring system 20 senses the waveform having the largest maximum pressure amplitude. Once the waveform having the largest maximum pressure amplitude is sensed and identified, or soon thereafter, the holddown pressure applied by holddown pressure assembly 36 is maintained at a constant or is preferably reduced. Because the application of an increasing holddown pressure by holddown pressure assembly 36 is terminated after the waveform having the largest maximum pressure amplitude is sensed, typically two individual waveforms following the sensed waveform having the largest pressure amplitude, holddown pressure assembly 36 does not apply a pressure to the underlying artery sufficient to occlude the underlying artery. As a result, monitoring system 20 senses the necessary parameters for determining blood pressure without occluding or pinching off the underlying artery. Because monitoring system 20 attains the necessary parameters for determining blood pressure without ever having to occlude the underlying artery and without having to necessarily apply pressure to the artery greater than a predicted diastolic blood pressure of the artery, monitoring system 20 continuously senses blood pressure with less discomfort to the patient. In addition, monitoring system 20 may be used in conjunction with a pulse oximeter.

Alternatively, once the waveform having the largest maximum pressure is sensed and identified, successive sweeps may alternatively have a varying hold down pressure applied until a preselected multiple of the mean hold down pressure of the waveform having the largest maximum pressure amplitude is reached. Preferably, each sweep range extends between the initial hold down pressure of 20 mmHg and a final hold down pressure of approximately 150% of the mean hold down pressure of the waveform having the largest maximum pressure amplitude during the previous sweep. In addition, the sweep range may alternatively have an initial hold down pressure of approximately 20 mmHg to a final hold down pressure having a preselected absolute value. Alternatively, the sweep could start at a high pressure and sweep low. As a safety measure, the pressure within pressure chamber (sensed by transducer 42) and interface chamber 210 (sensed by transducer 40) are continually monitored by monitor 26. If the ratio of the pressures within pressure chamber 116 and chamber 210 fall outside of a defined range of limits, an alarm is signaled.

After each hold down pressure sweep, blood pressure monitoring system 20 begins a successive new sweep to calculate new, successive blood pressure values. As a result, blood pressure monitoring system 20 continually measures blood pressure within the underlying artery without causing discomfort to the patient. As can be appreciated, the sweep range of hold down pressure applied by hold down pressure assembly 36 may have various initial and final points. Furthermore, the hold down pressure applied by hold down pressure assembly 36 may alternatively be intermittently varied. For example, the hold down pressure may be increased or decreased in a step-wise fashion.

Based upon sensed and sampled pressure waveform signals or data produced by transducer 40 and sent to monitor 26 during each sweep of hold down pressures, monitor 26 derives preselected parameters for calculating blood pressure values from the derived parameters and a stored set of coefficients. As indicated in FIG. 2, parameters may be derived directly from the absolute waveform pressures which vary as hold down pressure is varied over time. For example, parameter 720 is the diastolic pressure value of the uncorrected waveform having the largest maximum pressure amplitude value (waveform 500a). Although not absolutely necessary for determining a blood pressure value, parameters from waveforms following the waveform having the largest maximum pressure amplitude may be utilized. For example, parameter 710 is the systolic point of the uncorrected pressure waveform (waveform 500c) immediately following the uncorrected pressure waveform having the largest maximum pressure amplitude (waveform 500a). Parameter 730 is the diastolic pressure value of the uncorrected waveform (waveform 500c) immediately following the waveform (waveform 500a) having a largest maximum pressure amplitude or peak.

Such parameters may also be derived from the shape of the waveforms including a particular waveform's slope, absolute pressure at a selected sample point, a rise time to a selected sample point on a waveform and the hold down pressure corresponding to a particular sample point on a waveform. For example, the slopes along the portions of each individual waveform 500 may be determined. One parameter may constitute the holddown pressure applied to the underlying artery that corresponds to the point on the particular waveform having the maximum slope corrected amplitude. A slope corrected amplitude of an individual waveform is obtained by multiplying its amplitude with a maximum slope over all waveforms 500 and dividing the result with the slope corresponding to the individual waveform.

Parameters may also be derived from mean values of particular waveforms. For example, parameter 700 is the mean pressure of the uncorrected waveform 500a having the highest peak or maximum pressure. As can be appreciated, any of a variety of parameters may be derived from the absolute waveform pressures shown in FIG. 2. Parameters may further be based upon particular points or functions of the sample points.

FIG. 3 illustrates an example of how values or parameters of multiple waveforms 500 shown in FIG. 2 may be used to derive additional parameters. FIG. 3 shows several data points 510. Each data point 510 represents a selected waveform taken from the sweep shown in FIG. 2. Curve 520 is derived by fitting points 510 to a preselected function or relationship. Parameters such as the peak 530 are then derived from curve 520. As can be appreciated, various other parameters such as slope may also be derived from curve 520. Parameters derived from curve 520 are ultimately based upon pressure waveforms 500 shown in FIG. 2 which are produced from sensed pressure waveform data or signals from transducer 40. However, because curve 520 is derived using a plurality of waveforms 500, parameters derived from curve 520 represent the overall relationship between the plurality of waveforms 500. In other words, parameters derived from curve 520 represent the way in which the plurality of waveforms 500 (shown in FIG. 2) are related to one another. Data points 510 represent corrected, relative waveform pressures. As can be appreciated, functions such as curves may also be derived using absolute waveform pressure values which are shown in FIG. 2.

A waveform is "corrected" by subtracting the hold down pressure from the absolute pressure of the waveform to produce relative waveform pressures (otherwise known as amplitudes). Correcting a waveform eliminates characteristics of the waveform which result from a continuously increasing hold down pressure being applied to the artery during each waveform or cardiac cycle. FIG. 4 further illustrates other parameters which may be derived from waveform pressure values shown in FIG. 2. FIG. 4 illustrates waveform 600 selected from waveforms 500. Waveform 600 is preferably the waveform having the largest peak or maximum pressure amplitude. Alternatively, waveform 600 may be any of the waveforms 500 (shown in FIG. 2) such as waveforms immediately preceding or succeeding the waveform having the largest maximum pressure. As shown in FIG. 4, waveform 600 is corrected such that the beginning point 602 and an ending point 604 have the same absolute waveform pressure value. As further shown by FIG. 4, waveform 600 is horizontally and vertically scaled to eliminate gain. Preferably, waveform 600 is scaled from zero to twenty-one beginning at beginning point 602 and ending at ending point 604 of waveform 600 on the horizontal b axis. Preferably, waveform 600 is vertically scaled from zero to one beginning at its base and ending at its peak. Because waveform 600 is horizontally and vertically scaled, parameters may be derived from waveform 600 for calculating blood pressure values without the gain of the particular patient affecting the calculated blood pressure value. Gains are caused by the differences between the actual pressure exerted within the artery and the pressures sensed at the surface of the wrist or anatomy which is caused by varying characteristics of the intermediate tissue. Scaling waveform 600 eliminates any gains exhibited by individual patients. By using scaled values to locate corresponding points or waveform pressure amplitudes on waveform 600, points on waveform 600 uniformly correspond to the same points on waveforms exhibited by other patients.

As shown by FIG. 4, various parameters may be derived from scaled, corrected waveform 600. For example, parameters may constitute ratios of individual waveform pressure amplitudes at selected points along the horizontal b axis divided by the maximum waveform pressure amplitude or peak of the waveform. Such parameters may include ratios of the waveform pressure amplitude on waveform 600 which correspond to the scale value $b_3$, $b_9$, $b_{12}$, and $b_{13}$, points 608, 620, 624 and 622, respectively, divided by a maximum waveform pressure amplitude or peak of waveform 600 (point 606). A parameter may also constitute a time value representing a width of waveform 600 (represented by segment 614 between point 616 and 618 or by segment 626 between points 628 and 630 which corresponds to a preselected percentage of the maximum pressure amplitude or peak (point 606) of waveform 600. Time elapsed between points is determined by counting the number of samples taken by monitor 26 which lie above the points on waveform 600. As shown by FIG. 4, such parameters may include widths of waveform 600 at selected points along the vertical y axis, ratios of individual waveform pressure amplitudes at selected points along the horizontal b axis and the maximum amplitude of the waveform or the rise time or time elapsed from the start of waveform 600 at point 602 to a selected point along the vertical y axis.

Furthermore, a parameter may constitute the rise time or the lapse of time from the start of the waveform toward a particular point along the waveform 600 corresponding to a particular vertical scale value. For example, the lapsed time from the start of waveform 600 to a point 610 on waveform 600 which has a vertical height of approximately 0.18 that of a maximum pressure amplitude or peak (point 606) of waveform 600 is represented by segment 612 in FIG. 4. In addition, several other parameters may also be derived from waveform 600, such as slope and other shape characteristics.

III. Method of Ascertaining Relationship Between Selected Parameters and Blood Pressure Once the parameters to be used in calculating blood pressure values are selected, the relationship between the selected parameters and blood pressure must be ascertained to enable the blood pressure to be calculated based solely upon sensed values of the selected parameters. The relationship between a selected set of parameters and a blood pressure value is generally expressed by at least one function of the preselected set of parameters. Typically, in each ascertained function, each parameter from the set of parameters is multiplied by a corresponding ascertained coefficient. The functions including each parameters's corresponding coefficient represents the relationship between a particular parameter set and the resulting blood pressure value to be determined from the particular parameter set. The functions and coefficients are initially ascertained from clinical tests upon patients having known blood pressure values. Typically, the known blood pressure value is determined using the A-line method which is generally accurate, although difficult to set up, expensive and medically risky. As the blood pressure is determined using the A-line or other methods, sensor interface assembly 38 is positioned over the underlying artery of the patient. Hold down pressure assembly 36 applies a varying pressure to the artery of the patient having the known blood pressure value. As discussed above, transducer 40 produces sensed pressure waveform signals or data representing arterial pressure waveforms. Monitor 26 receives the produced sensed pressure waveform data and derives preselected parameters from the sensed pressure waveform data. As a result, a plurality of data sets are obtained. Each data set includes a known blood pressure and corresponding values for the preselected parameters. Functions and coefficients are then determined using each data set including the derived values of the selected parameters and the known blood pressure value. Each function and each coefficient corresponding to each selected parameter is based on the known blood pressure values and the derived parameters of the data sets. Preferably, several patients are clinically tested to attain a multitude of data sets for ascertaining the functions and coefficients.

Figure 5:
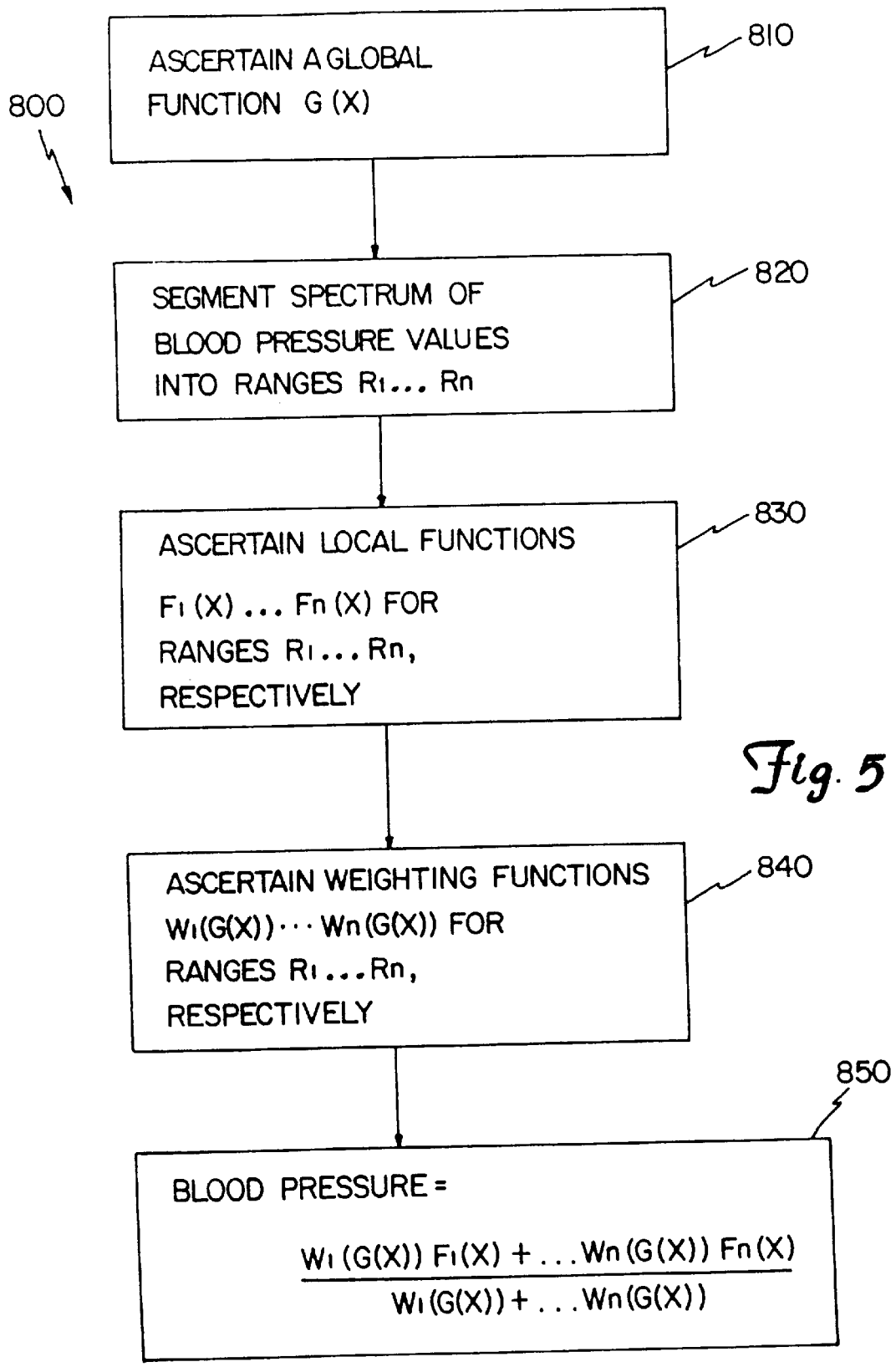
FIG. 5 is a flow chart of steps of a method of the present invention.
Figure 6:
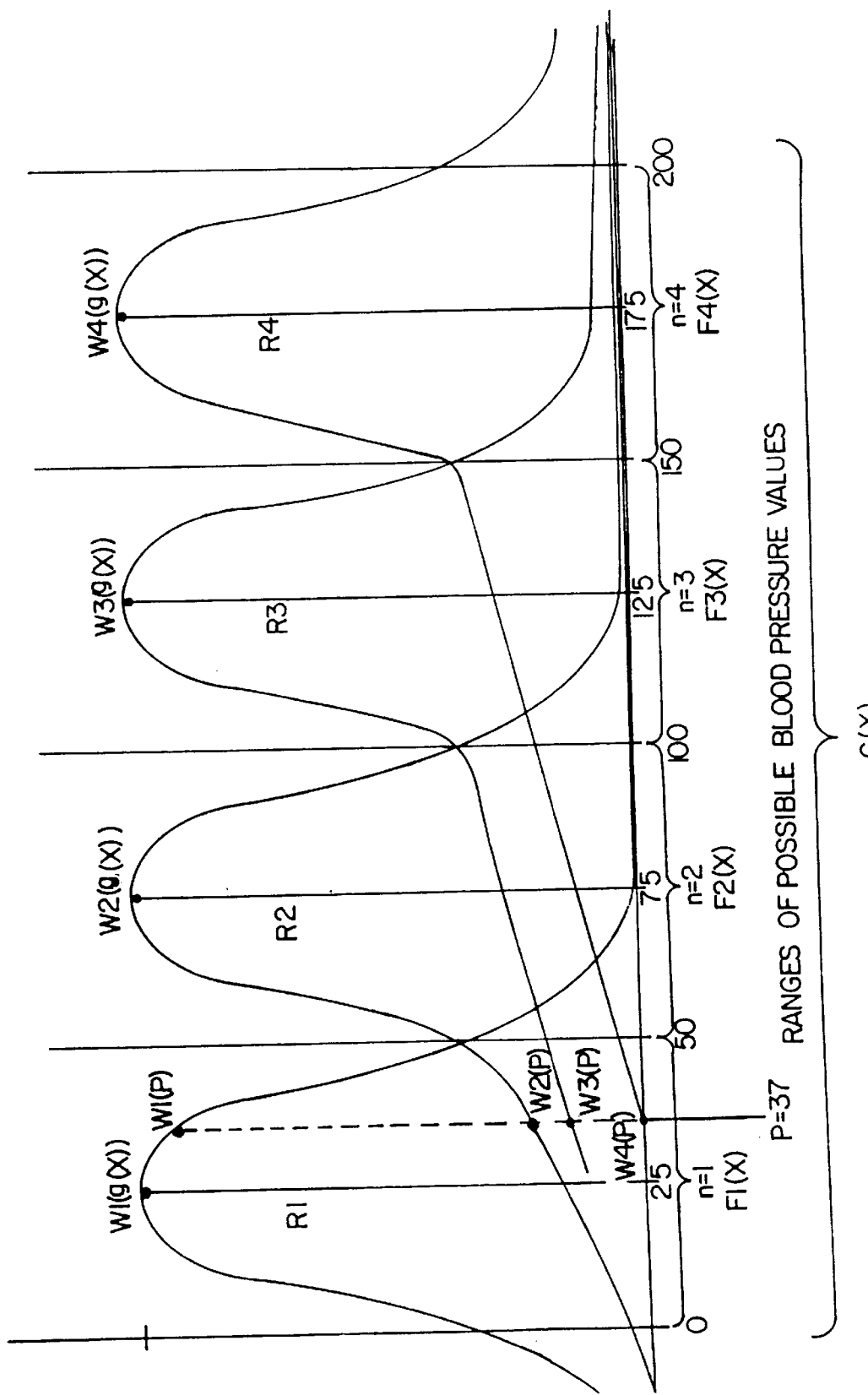
FIG. 6 is a graph illustrating the method of the present invention.

FIGS. 5 and 6 illustrate the general method by which the relationship between a preselected set of parameters and the blood pressure value is ascertained. FIG. 5 is a flow chart illustrating the steps by which the relationship between a preselected set of parameters and a blood pressure value is ascertained. FIG. 6 is a graph graphically illustrating a method of segmentation of the blood pressure values into a plurality of pressure ranges or subsets in order to ascertain a relationship between the preselected set of parameters and the blood pressure value for each pressure range. FIG. 5 illustrates a method 800 for ascertaining a relationship between the preselected set of parameters and the blood pressure value. Method 800 includes several steps indicated by blocks 810, 820, 830, 840 and 850. As indicated by block 810, a global function, G(x), based upon known blood pressure values across an entire spectrum of possible blood pressure values and each known blood pressure value's corresponding derived values for the preselected set of parameters is ascertained. For illustration purposes, the graph illustrated by FIG. 6 depicts possible blood pressure values ranging from 0 mmHg to 200 mmHg. As can be appreciated, the spectrum of possible blood pressure values for which a relationship between the blood pressure value and the parameters is ascertained may alternatively be larger or smaller. Furthermore, the range of possible blood pressure values may be established so as to have a lower end greater than 0 mmHg.

The global function G(x) is a function of the preselected set of parameters x and is depicted along an abscissa of the graph of FIG. 6. For example, in the illustration of FIG. 6, each known blood pressure value greater than or equal to about 0 mmHg and less than or equal to about 200 mmHg and its corresponding derived values for the preselected set of parameters are used to ascertain a global function. The global function may constitute any one of a variety of functions including both linear and non-linear functions. Preferably, the global function selected is one that minimizes a sum of differences between each known blood pressure value and a corresponding estimate of the blood pressure value based upon the known blood pressure value's corresponding derived values for the preselected set of parameters. The global function ascertained is used to estimate the blood pressure value based upon any derived values for the set of parameters, x. However, it has been discovered that a single global function is incapable of accurately estimating blood pressure values across an entire spectrum of possible blood pressure values.

As indicated by block 820, the entire spectrum of possible blood pressure values for a given patient is segmented or subdivided into a plurality of distinct subsets or ranges $R_1$ to $R_n$. Alternatively, the ranges may be selected so as to overlap one another. FIG. 6 illustrates a spectrum of possible blood pressure values from 0 to 200 mmHg segmented or subdivided into four distinct ranges $R_1$, $R_2$, $R_3$, $R_4$. As can be appreciated, the width of each range as well as the number of individual ranges may be varied as desired depending upon the amount of clinical data including known blood pressure values, the number and type of parameters used, the individual functions used to describe the relationship between the parameters and the blood pressure value and the level of accuracy desired. Although a spectrum of 0 to 200 mmHg pressure is illustrated in FIG. 6, the overall spectrum of possible blood pressure values may be increased or decreased as desired.

As indicated by block 830 in FIG. 5, once the spectrum of possible blood pressure values, for example, the spectrum of possible systolic blood pressure values, the spectrum of possible diastolic blood pressure values or the spectrum of possible mean blood pressure values, is segmented into a plurality of ranges, a distinct local function $F_i(x)$ is ascertained for each range i, i=1, . . . , n based upon the derived values for parameters of the selected set of parameters and the corresponding known blood pressure values within each range. For example, to ascertain a local function for the blood pressure value range centered around 75 mmHg, known blood pressure values centered around 75 mmHg, and their corresponding sensed values for parameters of the preselected set of parameters x are used to ascertain the distinct local function $F_2(x)$. The local function $F_i(x)$ selected for each range i=1, 2, . . . , n is preferably selected so as to minimize a sum of differences between each known blood pressure value and a corresponding estimate of the blood pressure value based upon the known blood pressure value's corresponding derived values for the parameters of the preselected set of parameters x. The local function $F_i(x)$ ascertained for each range i, i=1, . . . n estimates the blood pressure value based upon the preselected set of parameters x.

Once the global function and each distinct local function is ascertained, blood pressure may be non-invasively calculated based solely upon sensed and derived values for the preselected set of parameters x by using at least one of the local functions based upon the global function. Preferably, the method of the present invention determines or generates a final blood pressure estimate using a multitude of local functions and weighting each local function based upon a global blood pressure estimate of the global function. As a result, the method preferably includes ascertaining a weighting function $W_i(G(x))$ for each range i=1, . . . , n (or each local function $F_i(x)$) dependent upon the global blood pressure value estimate $G(x)$. This step is indicated by block 840. With this preferred method, each local function's estimate of blood pressure based upon the derived parameter value is used to calculate the final blood pressure value estimate. Each local function's estimate is weighted using the ascertained weighting function $Wi(G(x))$ based upon the global blood pressure value estimate $G(x)$. As a result, as indicated by block 850, the final blood pressure value estimate is the summation of the weighting function $W_i(G(x))$ multiplied by each local function, $F_i(x)$.

IV. Method of Determining Blood Pressure

Once the global function $G(x)$, the local functions $F_i(x)$ for each range i=1, . . . , n and the weighting functions $W_i(g(x))$ for each range i=1, . . . , n are ascertained, blood pressure may be non-invasively estimated using the ascertained relationship. For example, to estimate the blood pressure of a patient having an unknown blood pressure, wrist assembly 24 of blood pressure monitoring system 20 (illustrated in FIG. 1) is positioned over the underlying artery of the patient. A varying holddown pressure is applied to the artery and signals representing blood pressure pulses of the artery are sent to monitor 26 from wrist assembly 24 for waveform analysis. The waveform analysis extracts the plurality of waveform parameters x. Using the ascertained global function $G(x)$, monitoring system 26 calculates a global blood pressure value using the global function $G(x)$ and the derived values for the set of parameters x. Monitoring system 26 uses the global blood pressure value estimate to select and determine what percentage or weight of each local function $F(x)$ is used to estimate the blood pressure value. Based upon the derived values for the set of parameters x, the global blood pressure value estimate, each local function $F_i(x)$ and each weighting function $W_i(G(x))$, monitoring system 26 estimates the blood pressure value continuously and non-invasively. As illustrated by FIG. 6, to determine the weight of each of the distinct local functions $F(x)$ to be used to calculate blood pressure, a global blood pressure estimate $G(x)$ of the blood pressure is calculated using the derived parameter values and the ascertained global function $G(x)$. The global blood pressure estimate resulting from the global function is then used to weigh each one of the distinct ranges i=1, . . . , n and its corresponding local function $F_i(x)$ for final estimation of the blood pressure value. Each weighted local function $F_i(x)$ is preferably summed. Alternatively, each weighted local function $F_i(x)$ may be multiplied. Weighting each local function $F_i(x)$ enables a multitude of different functions to be used in calculating the blood pressure value with the impact of each function dependent upon the global blood pressure value estimate. For example, if the global blood pressure value estimate based upon sensed values of the set of parameters x is 100 mmHg, the blood pressure value estimated by monitor 26 is approximately $(0.02(F_1(x)+0.38(F_2(x))+0.38(F_3(x))+0.22(F_4(x))/(0.2+0.38+0.38+0.22)$. Other sensed values for the preselected set of parameters x may be similarly used to estimate blood pressure based solely upon the sensed values of the preselected set of parameters x.

Once ascertained, the global and local functions and their parameter coefficients are stored for use in non-invasively calculating blood pressure values of other patients without the necessity of using the more time consuming, expensive and risky A-line method and without using the generally more inaccurate conventional blood pressure measuring methods. The ascertained relationship between the preselected set of parameters and the blood pressure value enables blood pressure monitoring system 20 to calculate the same blood pressure value by simply sensing pressure data, deriving values for the same set of parameters and using the derived parameter values and the ascertained relationship. In particular, monitoring system 20 generates a global blood pressure estimate using the ascertained global function of the parameters, generates at least one local blood pressure estimate using at least one selected local function of the parameters, and weights and sums of the local blood pressure estimates using a weighting function based on the global blood pressure 20 estimate to produce a final blood pressure value. As a result, the blood pressure value may be accurately and easily determined non-invasively.

The global and local functions are preferably ascertained so as to be applicable for calculating blood pressure values from the derived waveform parameters of all patients. Alternatively, individualized sets of global and local functions may be used to calculate blood pressure values from derived waveform parameters of particular patients falling within a particular age group or other specialized groups. The global and local functions are preferably determined for use with the same blood pressure monitoring system as will be used to determine the particular blood pressure value of patients having unknown blood pressure values. However, as can be appreciated, the method of the present invention for determining blood pressure of an artery and for ascertaining a relationship between at least one parameter and a blood pressure value may be used in conjunction with any one of a variety of blood pressure monitoring systems including different sensor assemblies and hold down pressure assemblies.

Although the present invention has been described with reference to preferred embodiments, workers skilled in the art will recognize that changes may be made in form and detail without departing from the spirit and scope of the invention.

What is claimed is:

1. A method for ascertaining a relationship between at least one preselected parameter of at least one sensed pressure waveform and a blood pressure value for use in determining the blood pressure value, the method comprising:

ascertaining a first function based upon known blood pressure values and corresponding values of said at least one preselected parameter, wherein the first function estimates the blood pressure value;

segmenting possible blood pressure values into a plurality of subsets;

ascertaining a second function for each subset based upon known blood pressure values within each subset and corresponding sensed values of said at least one preselected parameter, wherein each distinct second function estimates the blood pressure value; and ascertaining the relationship between said at least one preselected parameter and the blood pressure value based upon the first function and at least one second function.

2. The method of claim 1 wherein the step of ascertaining the relationship includes:

ascertaining a weighting function for each second function dependent upon estimated blood pressure values of the first function.

3. The method of claim 2 including:

summing each weighted second function.

4. The method of claim 1 wherein the step of ascertaining a first function includes:

ascertaining a first function of said at least one preselected parameter that minimizes a sum of differences between each known blood pressure value and a corresponding estimate of the blood pressure value of the first function.

5. The method of claim 1 wherein the step of ascertaining a second function for each subset includes:

ascertaining a second function for each subset that minimizes a sum of differences between each known blood pressure value within its corresponding subset and a corresponding estimate of the blood pressure value of the second function.

* * * * *